(12) United States Patent
DiMatteo et al.

(10) Patent No.: US 8,591,564 B2
(45) Date of Patent: Nov. 26, 2013

(54) HYPOTUBE ENDOLUMINAL DEVICE AND METHOD

(75) Inventors: Kristian J. DiMatteo, Waltham, MA (US); Robert C. Thistle, Bridgewater, MA (US)

(73) Assignee: Lifeshield Sciences, LLC, Plano, TX (US)

( * ) Notice: Subject to any disclaimer, the term of this patent is extended or adjusted under 35 U.S.C. 154(b) by 8 days.

(21) Appl. No.: 12/975,001

(22) Filed: Dec. 21, 2010

(65) Prior Publication Data

US 2011/0125245 A1 May 26, 2011

Related U.S. Application Data

(62) Division of application No. 11/541,937, filed on Oct. 2, 2006, now Pat. No. 7,879,081, which is a division of application No. 10/139,127, filed on May 3, 2002, now Pat. No. 7,122,048.

(51) Int. Cl.
*A61F 2/06* (2013.01)

(52) U.S. Cl.
USPC ........................................ 623/1.11

(58) Field of Classification Search
USPC ........... 623/1.19, 1.42, 1.11, 1.12, 1.13, 1.15, 623/1.23, 1.44; 600/200
See application file for complete search history.

(56) References Cited

U.S. PATENT DOCUMENTS

| | | | |
|---|---|---|---|
| 4,503,569 A * | 3/1985 | Dotter ......................... | 623/1.19 |
| 4,887,996 A * | 12/1989 | Bengmark .................... | 604/500 |
| 5,207,644 A | 5/1993 | Strecker | |
| 5,234,456 A * | 8/1993 | Silvestrini .................... | 623/1.2 |
| 5,256,146 A * | 10/1993 | Ensminger et al. ........... | 604/104 |
| 5,413,560 A | 5/1995 | Solar | |
| 5,500,013 A | 3/1996 | Buscemi et al. | |
| 5,523,092 A * | 6/1996 | Hanson et al. ................ | 424/423 |
| 5,536,274 A * | 7/1996 | Neuss ......................... | 623/1.22 |
| 5,628,784 A | 5/1997 | Strecker | |
| 5,882,335 A | 3/1999 | Leone et al. | |
| 5,891,108 A * | 4/1999 | Leone et al. ................. | 604/264 |
| 6,015,422 A | 1/2000 | Kerr | |
| 6,019,785 A | 2/2000 | Strecker | |

(Continued)

FOREIGN PATENT DOCUMENTS

| | | |
|---|---|---|
| WO | 96/26682 | 9/1996 |
| WO | 00/69367 | 11/2000 |
| WO | 02/05731 | 1/2002 |

OTHER PUBLICATIONS

International Search Report for corresponding international application, mailing date Sep. 5, 2003.

*Primary Examiner* — S. Thomas Hughes
*Assistant Examiner* — Julie A Szpira
(74) *Attorney, Agent, or Firm* — Brooks, Cameron & Huebsch, PLLC

(57) ABSTRACT

A self-expanding endoluminal device comprising a tubular filamentary member having a hollow core for receiving a guidewire, the tubular member having a straightened configuration with the guidewire in the hollow core, a shape memory configuration without the guidewire in the hollow core, and an extension, optionally severable, accessible from outside of the body. The hollow core may be adapted to contain and elute or permanently contain a substance, which may be injected through the extension. A delivery system includes the guidewire, and a deployment method includes deployment with a proximal end of the extension accessible from outside of the body.

11 Claims, 5 Drawing Sheets

(56) References Cited

U.S. PATENT DOCUMENTS

| | | | |
|---|---|---|---|
| 6,059,825 A | 5/2000 | Hobbs et al. | |
| 6,071,305 A * | 6/2000 | Brown et al. | 623/1.43 |
| 6,095,990 A * | 8/2000 | Parodi | 600/585 |
| 6,096,070 A | 8/2000 | Ragheb et al. | |
| 6,102,918 A | 8/2000 | Kerr | |
| 6,168,620 B1 | 1/2001 | Kerr | |
| 6,193,746 B1 | 2/2001 | Strecker | |
| 6,221,100 B1 | 4/2001 | Strecker | |
| 6,258,121 B1 | 7/2001 | Yang et al. | |
| 6,319,276 B1 * | 11/2001 | Holman et al. | 623/1.11 |
| 6,338,736 B1 * | 1/2002 | Boosfeld et al. | 606/191 |
| 6,358,556 B1 | 3/2002 | Ding et al. | |
| 6,364,856 B1 | 4/2002 | Ding et al. | |
| 6,485,524 B2 | 11/2002 | Strecker | |
| 6,716,238 B2 | 4/2004 | Elliott | |
| 6,743,198 B1 * | 6/2004 | Tihon | 604/104 |
| 6,752,829 B2 * | 6/2004 | Kocur et al. | 623/1.42 |
| 7,011,682 B2 * | 3/2006 | Lashinski et al. | 623/2.37 |
| 7,052,511 B2 | 5/2006 | Weldon et al. | |
| 7,201,738 B1 * | 4/2007 | Bengmark | 604/170.03 |
| 2001/0003801 A1 * | 6/2001 | Strecker | 623/1.11 |
| 2009/0024209 A1 * | 1/2009 | Ozdil et al. | 623/1.42 |

* cited by examiner

HYPOTUBE ENDOLUMINAL DEVICE AND METHOD

CROSS-REFERENCE TO RELATED APPLICATIONS

This application is a divisional of U.S. patent application Ser. No. 11/541,937, filed Oct. 2, 2006, which is a divisional of U.S. patent application Ser. No. 10/139,127, filed May 3, 2002, now U.S. Pat. No. 7,122,048, the entire contents of which are incorporated herein by reference.

TECHNICAL FIELD

This invention relates generally to medical implants and, more specifically, to medical implants made from hypotubes capable of containing substances therein.

BACKGROUND OF THE INVENTION

Medical implants for placement in a human or other animal body are well known in the art. One class of medical implants comprises endoluminal devices such as stents, stent-grafts, filters, coils, occlusion baskets, valves, and the like. As is known in the art, a stent is typically an elongated device used to support an intraluminal wall. Such a stent may also have a prosthetic graft layer of fabric or covering lining the inside and/or outside thereof. Such a covered stent is commonly referred to in the art as an intraluminal prosthesis, an endoluminal or endovascular graft (EVG), or a stent-graft. Although stent-grafts may be used in any number of applications, the use of stent-grafts for repairing abdominal aortic aneurysms (AAA) is an area of particular interest. Other devices, such as filters or occlusion devices (also known as wire clusters), may have similar structures to stents and may be placed in a body lumen by similar methods. As used herein, the term "endoluminal device" refers to covered and uncovered stents, filters, wire clusters, and any other device that may be placed in a lumen. The term "stent" as used herein is a shorthand reference referring to a covered or uncovered stent. Typical mechanisms for expansion of endoluminal devices include spring elasticity, balloon expansion, and self-expansion of a thermally or stress-induced return of a memory material to a pre-conditioned expanded configuration.

Endoluminal devices are sometimes coated on their outer surfaces with a substance such as a drug releasing agent, growth factor, or the like. U.S. Pat. No. 5,500,013 to Buscemi et al. is just one example of numerous patents relating to endoluminal devices having such coatings. Stents have also been developed comprising a hollow tubular wire with perforations for injecting drugs into the hollow wire and through the perforations into the body lumen, such as are disclosed by Leone et al. in U.S. Pat. No. 5,882,335 and No. 5,891,108, incorporated herein by reference.

Traditionally, an endoluminal device, such as a stent-graft deployed in a blood vessel at the site of a stenosis or aneurysm, is implanted endoluminally, i.e. by so-called "minimally invasive techniques" in which the device, restrained in a radially compressed configuration by a sheath or catheter, is delivered by a delivery system or "introducer" to the site where it is required. The introducer may enter the body from an access location outside the body, such as through the patient's skin (percutaneous methods), or by a "cut down" technique in which the entry blood vessel is exposed by minor surgical means. The term "proximal" as used herein refers to portions of the stent or delivery system relatively closer to the end of the delivery system extending outside of the body, whereas the term "distal" is used to refer to portions relatively farther from this outside end. When the introducer has been threaded into the body lumen to the deployment location, the introducer is manipulated to cause the endoluminal device to be ejected from the surrounding sheath or catheter in which it is restrained (or alternatively the surrounding sheath or catheter is retracted from the endoluminal device), whereupon the endoluminal device expands to a predetermined diameter at the deployment location, and the introducer is withdrawn.

Over the past several years there has been a drive toward developing low-profile endoluminal devices that can be introduced using the more preferred percutaneous approach, as the cut down approach has been found to have increased risk of complication associated with it. Thus, there is a continued need in the art for developing endoluminal devices having the lowest-possible profile and having as many positive attributes as possible.

SUMMARY OF THE INVENTION

One aspect of the invention comprises a self-expanding endoluminal device, such as but not limited to a stent, a filter, or an occlusion device, comprising at least one tubular filamentary member having a hollow core for receiving a guidewire, the tubular member having a straightened configuration with the guidewire in the hollow core and a shape memory configuration without the guidewire in the hollow core. Another aspect of the invention comprises an endoluminal device and delivery system for deploying the endoluminal device in a body lumen from a proximal point outside of the body lumen. The device and delivery system comprise at least one guidewire and the self-expanding endoluminal device, the device comprising at least one tubular filamentary member having a hollow core for receiving the guidewire. The tubular member has a straightened configuration with the guidewire in the hollow core and a shape memory configuration without the guidewire in the hollow core.

The system may further comprise a substance contained within the hollow core of the tubular filamentary member, and may even further comprise means for injecting the substance into the hollow core. The tubular filamentary member may be adapted to permanently contain the substance in the hollow core, such as but not limited to embodiments in which the substance comprises a radioactive substance, a contrast agent, or a substance that undergoes a change in viscosity or state once the device has been implanted in the body. In another embodiment, the tubular filamentary member may comprise one or more openings through which the substance can be eluted from the hollow core, such as but not limited to embodiments in which the substance is a biologically or pharmacologically active agent. In one embodiment, the tubular filamentary member may be coated with a coating material that comprises a biologically or pharmacologically active agent, a coating that the substance inside the hollow core is capable of leaching through, or both. In another embodiment, the guidewire may be a hollow core guidewire for use in injecting the substance into the tubular member.

In one embodiment the device may comprise a proximal extension of the tubular filamentary member extending to a proximal end outside of the body lumen, and may even further comprise a severable connecting element between the proximal extension and the endoluminal device. The connecting element may be severable, for example, through application of a mechanical force and/or an electric current originating at or near the proximal end of the proximal extension, or through dissolution by injection of a solvent into the tubular filamentary member.

In one embodiment, the endoluminal device may comprise a plurality of filamentary members attached together, at least one of more of which may be tubular filamentary members. The device and delivery system may further comprise a plurality of parallel guidewires, each guidewire for engaging one of the plurality of tubular filamentary members. At least one of the tubular filamentary members may at least partially contain a substance in its hollow core. The substance-containing tubular member may be a member adapted for being advanced over a guidewire, or a member not adapted for being advanced over a guidewire.

In one aspect of the invention, the endoluminal device comprises a graft attached at or near a distal end of the tubular filamentary members. The device may comprise a first tubular filamentary member having a straightened configuration and a shape-memory configuration attached at or near a distal end of the graft, and a second tubular filamentary member having a straightened configuration and a shape-memory configuration for engaging a proximal end of the graft. In one embodiment, the graft comprises a trunk section, a first leg, and a second leg, and the device comprises a first tubular filamentary member having a straightened configuration and a shape-memory configuration attached at or near the distal end of the graft for holding the trunk section against a body lumen, and a second tubular filamentary member having a straightened configuration and a shape-memory configuration for engaging a proximal end of the first leg of the graft. A third tubular filamentary member having a straightened configuration and a shape-memory configuration engages a proximal end of the second leg of the graft.

Another aspect of the invention comprises a method of deploying an endoluminal device in a body lumen from a proximal point outside of the body lumen. The method comprises the step of providing a delivery system comprising a guidewire having an outer diameter, and a self-expanding endoluminal device comprising at least one tubular filamentary member having a straightened configuration for mounting on the guidewire and a shape memory configuration for deployment in the body lumen. Next, at least the guidewire is advanced into the body lumen to a deployment location, and the guidewire is used to deploy the tubular filamentary member in its shape-memory configuration in the deployment location. Where the step of advancing the guidewire comprises advancing the guidewire with the tubular filamentary member mounted thereon, the deployment step comprises retracting the guidewire and/or advancing the tubular filamentary member off of a distal end of the guidewire into the deployment location. Where the step of advancing the guidewire comprises advancing the guidewire without the tubular filamentary member mounted thereon, the deployment step comprises advancing the tubular filamentary member over the guidewire and off of a distal end of the guidewire into the deployment location. The method may also comprise injecting a substance into the tubular filamentary member. The method may then also comprise the tubular filamentary member eluting the substance into the body lumen. In a method where the endoluminal device comprises a proximal extension of the tubular filamentary member extending to a proximal end outside of the body lumen, the injecting step comprises injecting the substance into the tubular filamentary member through the proximal extension. Where the endoluminal device comprises a severable connecting element between the proximal extension and the endoluminal device, the method further comprises severing the proximal extension from the tubular filamentary member at the severable connecting element, such as but not limited to, by applying a mechanical force and/or an electric current originating at or near the proximal end of the proximal extension to sever the proximal extension from the tubular filamentary member, or injecting a solvent into the proximal extension to sever the proximal extension from the tubular filamentary member by dissolving the severable connecting element.

It is to be understood that both the foregoing general description and the following detailed description are exemplary, but not restrictive, of the invention.

BRIEF DESCRIPTION OF THE DRAWINGS

The invention is best understood from the following detailed description when read in connection with the accompanying drawing, in which.

DETAILED DESCRIPTION OF THE INVENTION

Figure 1A:
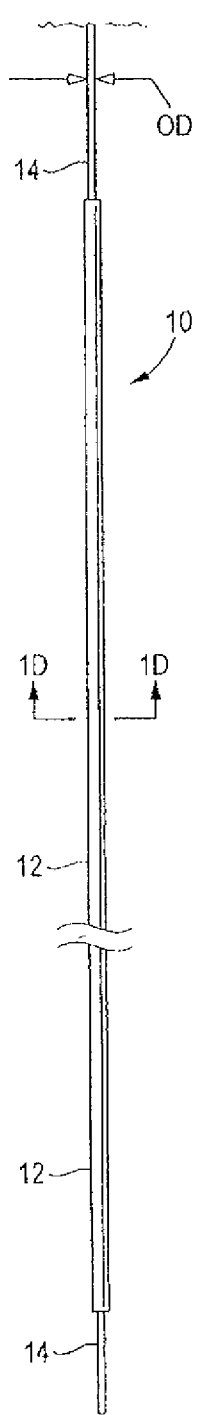
FIG. 1A is a plan view of an exemplary endoluminal device and delivery system of the present invention.
Figure 1B:
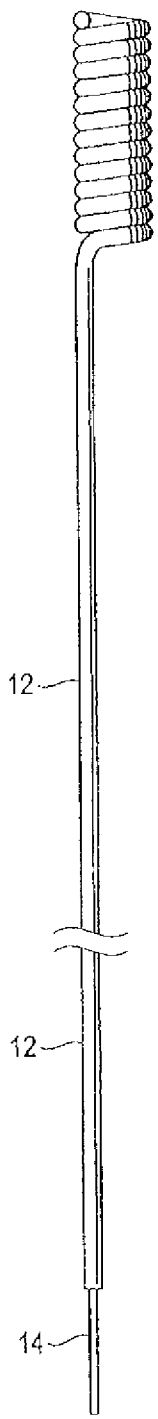
FIG. 1B is a plan view of the device and system of FIG. 1A after partial deployment of the device.

The invention will next be illustrated with reference to the figures wherein the same numbers indicate similar elements in all figures. Such figures are intended to be illustrative rather than limiting and are included herewith to facilitate the explanation of the apparatus of the present invention.

Referring now to FIGS. 1A-1D, there is shown an embodiment of the present invention comprising an endoluminal device and delivery system 10 comprising the endoluminal device 12 and a guidewire 14. Device 12 comprises a tubular member having a straightened configuration (shown in FIG. 1A mounted on guidewire 14) and a shape memory configuration (shown in FIG. 1C) in the shape of a helical coil having a generally cylindrical envelope. The tubular member has a hollow core 34 with an interior diameter ID greater than the guidewire outer diameter OD by an amount sufficient to allow the tubular member to be placed on the guidewire in the straightened configuration. The tubular member is designed to assume the shape-memory configuration after the guidewire has been removed from the hollow core.

In some embodiments, the tubular member may comprise a hypotube. As is known in the art, a hypotube is a hollow metal tube of very small diameter, of the type typically used in manufacturing hypodermic needles (hence the name hypotube). Members 32 may comprise any type of hollow tube, however, and are not limited only to tubes considered in the art to be hypotubes. For example, the tubular member may comprise a plurality of filamentary members braided to simulate a hypotube (not shown), such as is known in the art with respect to manufacture of guidewires.

The use of a tubular member as a stent has a number of advantages. First of all, because the tubular member may be advanced over a guidewire, rather than being held within a larger diameter sheath as is traditionally done in the art, the tubular member has an extremely low profile during deployment, which is advantageous for percutaneous methods of deployment. Another benefit of using a tubular member, is the capability of injecting or providing a drug into the tubular member before, during, or after deployment, as is described herein.

Figure 2A:
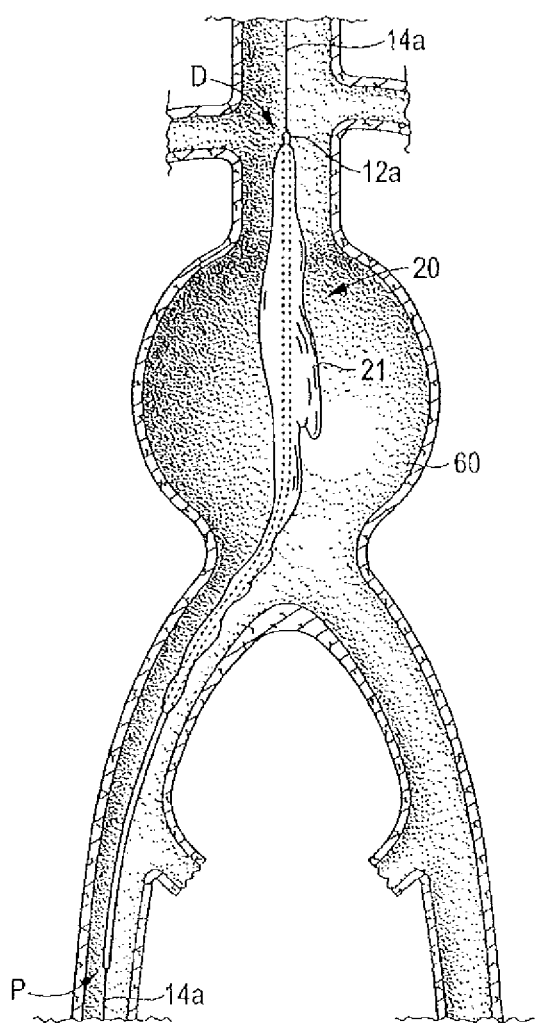
FIG. 2A is a cutaway view of a body lumen, showing deployment of an embodiment in which the endoluminal device comprises a graft attached to the tubular member.
Figure 2B:
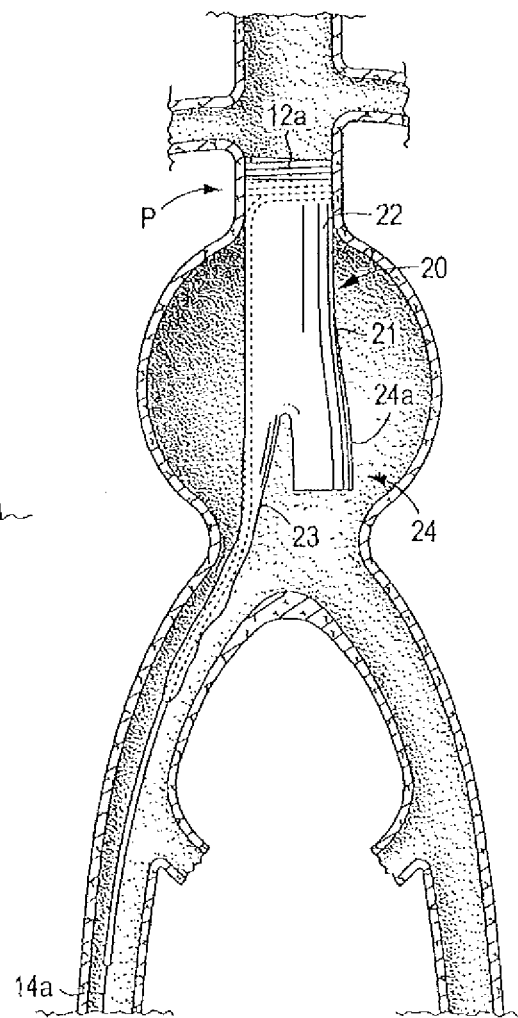
FIG. 2B is a view of the endoluminal device of FIG. 2A, after partial deployment.
Figure 2C:
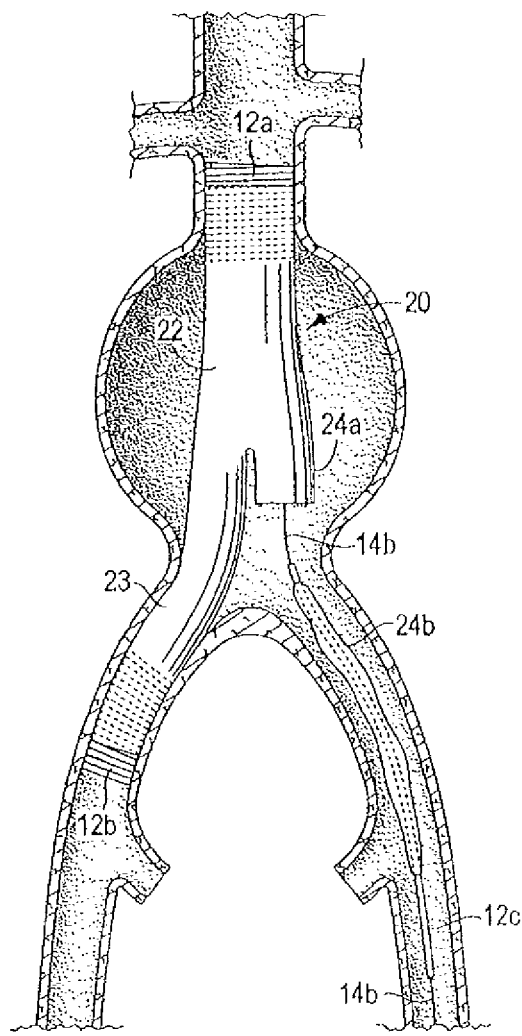
FIG. 2C is a view of the endoluminal device of FIG. 2B, after deployment of a second tubular member to hold one leg in place, and showing installation of a third tubular member in progress.

Referring now to FIGS. 2A-2C, there is shown another embodiment of the invention in which endoluminal device 20 comprises not only tubular member 12a, which is mounted on guidewire 14a, but also a graft 21 attached at or near distal end D of the tubular member. Graft 21 may comprise any material known in the art for use in endoluminal devices, including but not limited to polyester, ePTFE (expanded PolyTetraFluoro-Ethylene), silk, and/or urethane. Graft 21 may be attached to the tubular member by an adhesive bond, a suture, or any other mechanism known in the art.

Figure 2D:
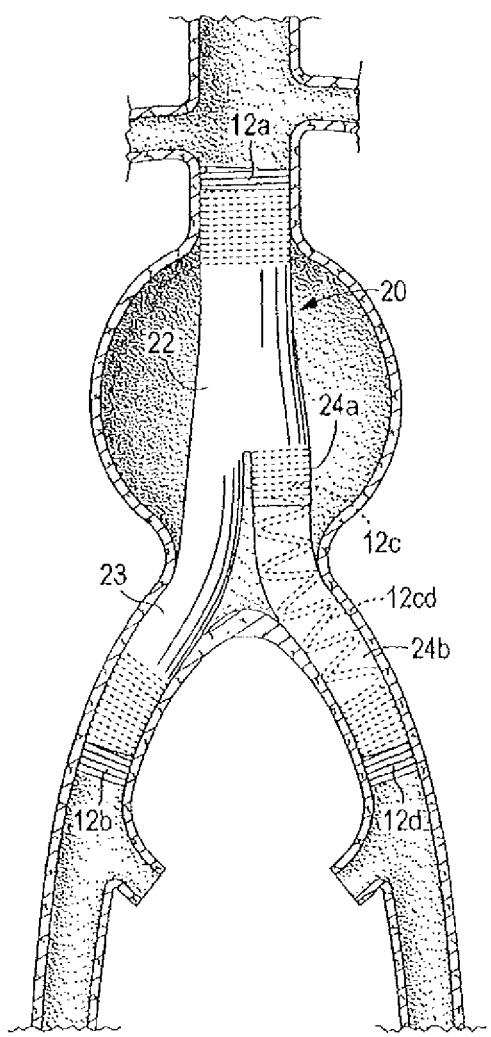
FIG. 2D is a view of the endoluminal device of FIG. 2C, after deployment, showing four tubular members holding two modular grafts in an assembled configuration.

As shown in FIGS. 2A-2D, graft 21 is a bifurcated graft comprising a trunk section 22, a first leg 23, and a second leg 24, and is adapted for repair of abdominal aortic aneurysms (AAA) 60. Grafts are not limited to bifurcated designs, however, and may have more than two legs or no legs. Likewise, bifurcated designs are not limited to AAA applications. Graft 21 may be a non-modular graft, or a modular graft such as shown in FIGS. 2B-2D, in which trunk section 22, relatively longer first leg 23, and relatively shorter female portion 24a of second leg 24 comprise a first modular member, and male extended portion 24b of second leg 24 comprises a second modular member. A non-modular design may comprise a graft comprising a trunk section and two legs of equal size.

One method of deploying device 20 comprises maneuvering first tubular member 12a over guidewire 14a (or maneuvering guidewire 14a through the lumen with the tubular member already mounted on the guidewire) until a desired deployment location is reached. Then, guidewire 14a is retracted, and/or first tubular member 12a is advanced past the distal end of the guidewire until the first tubular member is fully deployed, as shown in FIG. 2B. The first tubular member 12a may be advanced or using a pusher or stabilizer (not shown) mounted proximally of the tubular member, as such devices are known generally in the art. Where tubular member 12a has a high degree of "foreshortening" (a measure of the change in length between the shape memory configuration and the straightened configuration), such as is depicted for in the devices depicted in FIGS. 1A-2C, retraction of the guidewire and advancement of the pusher may be coordinated using a device similar to that shown and described in U.S. patent application Ser. No. 10/115,669, filed on Apr. 4, 2002, by James Weldon and Ilya Yampolsky, assigned to the common assignee of this application, and incorporated herein by reference. First tubular member 12a may have a construction similar to the design shown in FIG. 8 and described in detail below, in which a supply tube 82 is attached to its proximal end P of the tubular member and extends proximally therefrom, or member 12a may have no such supply tube.

Figure 3:
FIG. 3 is an illustration of an exemplary endoluminal device in which a second tubular member is positioned as a pusher for a first tubular member.

After first tubular member 12a has been deployed to secure a distal portion of truck section 22 of graft 21 against the body lumen, a second tubular member 12b may be deployed to secure a proximal portion of first leg 23, as shown in FIG. 2C. In one embodiment, first tubular member 12a and second tubular member 12b may be mounted on a single guidewire 14a. In one such embodiment, second tubular member 12b may be positioned proximally of first tubular member 12a such that the second tubular member serves as a pusher for the first tubular member, as shown in FIG. 3. In another embodiment (not shown), the first tubular member may be mounted on a first guidewire and the second tubular member mounted on a second guidewire. The first and second guidewires may have features that enable rapid guidewire exchange as are known in the art, for example, such as are described in U.S. Pat. No. 6,095,990, issued to Dr. Juan Parodi on Aug. 1, 2000, and incorporated herein by reference.

To deploy male extended portion 24b of modular graft 21, guidewire 14b may be advanced through the opposite iliac artery through which guidewire 14a was advanced. Tubular member 12c with attached graft 24b may then be advanced over guidewire 14b into a mating configuration with female portion 24a of leg 24. As shown in FIG. 2D, member 12c secures the distal end of male portion 24b to female portion 24a, while tubular member 12d secures the proximal end of portion 24b to the artery. Thus, tubular members 12c and 12d may be similarly configured on a single guidewire as shown in FIG. 3, or on separate guidewires. Also, members 12c and 12d may be end portions of a single tubular member that coils along the entire length of graft portion 24b, having a distal end portion 12c, a proximal end portion 12d, and a middle portion 12cd (shown in dashed lines). Such a single tubular member may comprise a helical pitch in portion 12cd that is larger than in portions 12c and 12d. Likewise, members 12a and 12b may comprise a single tubular member, if desired.

Referring now to FIGS. 4A-5B, there is shown one embodiment of the present invention comprising a stent 30 having a filamentary architecture, each member 32 comprising a hollow tube. As shown in FIG. 4B, each member 32 may have its own guidewire 14, forming a plurality of parallel guidewires in the straightened configuration. In alternate embodiments (not shown), however, less than all of the members may have guidewires and/or less than all of the members may be hollow. For example, in one embodiment (not shown), only one of the members 32 may be hollow, and a single guidewire 14 may be used for advancement of stent 30 into a deployment position. In another embodiment (not shown), all of the members may be hollow, but less than all but more than one of them may be used for advancing the stent into position over respective guidewires. Any of the myriad combinations of hollow, non-hollow, guidewire-advancing, and non-guidewire-advancing members may be used for forming stents in any number of architectures. Designs with multiple filaments may be held in a compressed configuration by a crocheted meshwork having a drawstring, such as is described in U.S. Pat. No. 6,019,785 to Strecker, incorporated herein by reference.

Figure 4A:
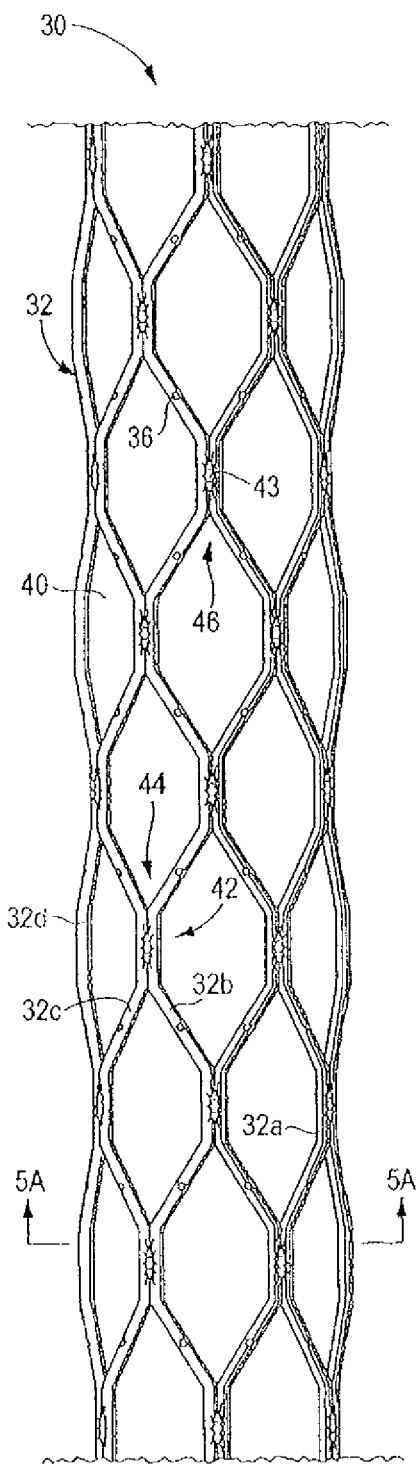
FIG. 4A is a plan view of an exemplary endoluminal device comprising a plurality of filamentary members in a hexagonal cell architecture, in an expanded configuration.
Figure 4B:
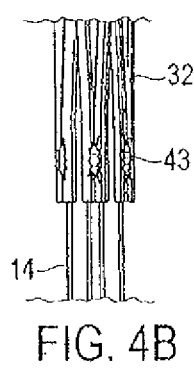
FIG. 4B is a plan view of a proximal portion of the device of FIG. 4A in a straightened configuration mounted on a plurality of guidewires.

In multi-filament embodiments, one or more of the hollow members may contain a substance therein. For embodiments in which less than all of the hollow members are advanced over guidewires, one option is to use the non-guidewire-advancing members for containing the substance. The hollow members that are advanced over guidewires may also contain the substance, however, which is true with respect to multiple member embodiments such as is shown in FIGS. 4A and 4B, and with respect to single member embodiments such as is shown in FIGS. 1A-D, for example.

Figure 5A:
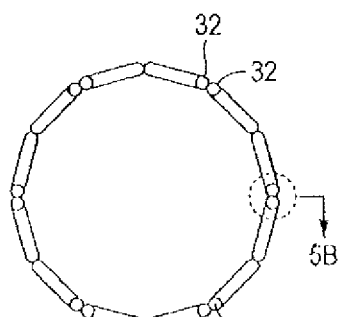
FIG. 5A is a cross sectional view of the stent of FIG. 4A taken across lines 5A-5A.
Figure 5B:
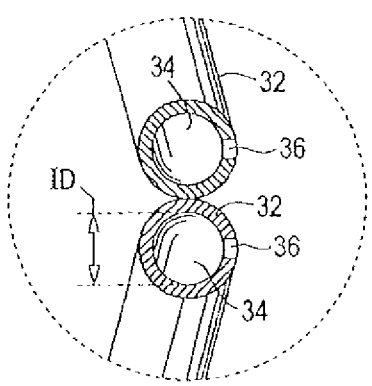
FIG. 5B is a magnified portion of the encircled portion of FIG. 5A.

In some embodiments, it may be desired for the substance contained in the tubular member or members to elute out of the members. Accordingly, tubular members 32 may comprise a plurality of openings 36, such as micro-machined or laser-drilled holes, for eluting the substance once the endoluminal device is placed in a body lumen, as shown in FIG. 5B. The eluted substance contained in the hollow tubes 32 may be any substance useful for delivering to the body lumen. For example, the substance may comprise a biologically or pharmacologically active substance. In one embodiment, the biologically or pharmacologically active substance may comprise a gelatinous suspension to prevent premature loss of the substance from the tubes until the device has been implanted in a body. Methods of making gelatinous carriers for biologically or pharmacologically active ingredients are well known in the art.

The term "biologically or pharmacologically active substance" refers to any substance, whether synthetic or natural, that has a pharmacological, chemical, or biological effect on the body or a portion thereof. Suitable biologically or pharmacologically active materials that can be used in this invention include without limitation glucocorticoids (e.g. dexamethasone, betamethasone), antithrombotic agents such as heparin, cell growth inhibitors, hirudin, angiopeptin, aspirin, growth factors such as VEGF, antisense agents, anti-cancer agents, anti-proliferative agents, oligonucleotides, antibiotics, and, more generally, antiplatelet agents, anti-coagulant agents, anti mitotic agents, antioxidants, antimetabolite agents, and anti-inflammatory agents may be used. Antiplatelet agents can include drugs such as aspirin and dipyridamole. Aspirin is classified as an analgesic, antipyretic, anti-inflammatory and antiplatelet drug. Dipyridamole is a drug similar to aspirin in that it has anti-platelet characteristics. Dipyridamole is also classified as a coronary vasodilator. Anticoagulant agents may include drugs such as heparin, protamine, hirudin and tick anticoagulant protein. Anti-cancer agents may include drugs such as taxol and its analogs or derivatives. Taxol is also classified as a cell-growth inhibitor. Antioxidant agents may include probucol. Anti-proliferative agents may include drugs such as amlodipine and doxazosin. Antimitotic agents and antimetabolite agents may include drugs such as methotrexate, azathioprine, vincristine, vinblastine, 5-fluorouracil, adriamycin and mutamycin. Antibiotic agents can include penicillin, cefoxitin, oxacillin, tobramycin, and gentamicin. Suitable antioxidants include probucol. Also, genes or nucleic acids, or portions thereof may be used. Such genes or nucleic acids can first be packaged in liposomes or nanoparticles. Furthermore, collagen-synthesis inhibitors, such as tranilast, may be used.

Additional biologically or pharmacologically active substances and carriers for these substances are listed in U.S. Pat. No. 6,364,856; No. 6,358,556; and No. 6,258,121; all of which are incorporated herein by reference. In addition to disclosing additional active substances, these patent references disclose polymer materials impregnated with active substances for use as coatings on the outside of medical devices to provide controlled delivery of the active substances. These same polymer materials impregnated with active substances as disclosed in the '856, '556, and '121 patents may be used on the inside of a tubular member in any of the devices of the present invention. A combination of an active substance inside the tubular member and an outer coating comprising an active substance may also be used. The active substance inside the tubular member may be the same as in the outer coating, or different, and the release characteristics of the substance inside the tubular member may be the same as the release characteristics of the outer coating, or different. For example, it may be desired to have a first substance in the outer coating that is released more quickly than a second substance inside the tubular member.

Figure 6:
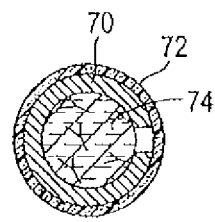
FIG. 6 is a cross-section of a tubular, perforated endoluminal device having a coating for allowing effusion of an internally contained substance.

In the exemplary embodiment shown in FIG. 6, a perforated tube 70 comprises an outer coating 72. This outer coating may be a coating impregnated with a biologically or pharmacologically active substance, such as described above, for use in tandem with a biologically or pharmacologically active substance 74 inside the perforated tube, it may be a layer that controls the release of substance 74, or both. For example, coating 72 may comprise a substance such as but not limited to silicone or corethane, which allows substance 74 to leach through the coating material over time to provide a more controlled release of the substance. The coating controls the effusion of the substance out of the tube and may prevent effusion prior to implantation of the device in the body. Suitable materials and methods for coating a medical device with materials to control release of biologically or pharmacologically active substances through the coating are listed in U.S. Pat. No. 6,096,070, incorporated herein by reference. In particular, the '070 patent lists polymers including but not limited to polyamide, polymers of parylene or derivatives thereof, poly(ethylene oxide), poly(ethylene glycol), poly(propylene oxide), silicone based polymers, polymers of methane, tetrafluoroethylene or tetramethyldisiloxane and polymers derived from photopolymerizeable monomers. Although not limited to only the materials generally or specifically listed above or listed in the '070 patent, embodiments of the present invention may utilize any of the materials so listed.

Exemplary stent 30 shown in FIG. 4A has a hexagonal cell architecture comprising a plurality of cells 40 defined by a plurality of members 32a, 32h, 32c, etc. positioned adjacent one another with parallel portions 42, divergent portions 44, and convergent portions 46 for each pair of adjacent members. The adjacent members may be attached to one another at one or more of the parallel portions 42, such as by an adhesive bond 43, a suture, a soldered joint, a braised joint, a weld, such as a laser weld, or any type of affixation made by any method known in the art. The type of affixation may be dependent upon the type of member. For example, a hollow member designed for advancing over a guidewire or for containing a substance may be more preferably attached to adjacent members by an adhesive bond or other non-destructive technique rather than, for example, a weld, to assure that the affixation technique does not compromise the ability of the hollow member to adequately slide over the guidewire or for the substance to fill the entire length of the tube when injected from one end, if desired. Attachments between non-hollow tubes, however, such as in a multi-filament stent, typically do not raise such issues and are more unlimited in affixation technique.

Figure 7:
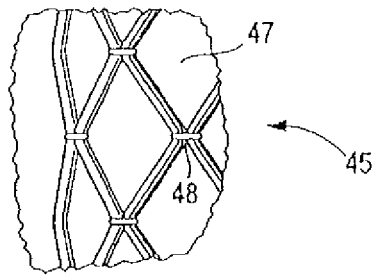
FIG. 7 a plan view of an exemplary endoluminal device comprising a plurality of filamentary members in a diamond-shaped cell architecture.

Other stent polygonal cell stent architectures are also well-suited for use with multiple hollow tubes advanced over multiple guidewires. For example, diamond shaped polygonal cells 47 as shown in the architecture of stent 45 as shown in FIG. 7, comprise a plurality of apices 48 abutting one another, with at least some of the apices are attached to one another, such as with a suture 48. Any attachment method known in the art may be used however, subject to the considerations discussed above with respect to the hexagonal cell architecture. Although shown with a hexagonal cell architecture in FIG. 4A and with a diamond-shaped polygonal cell architecture in FIG. 7, the endoluminal device is not limited to any particular geometry or architecture, and may comprise any suitable pattern of one or more hypotubes.

Figure 8:
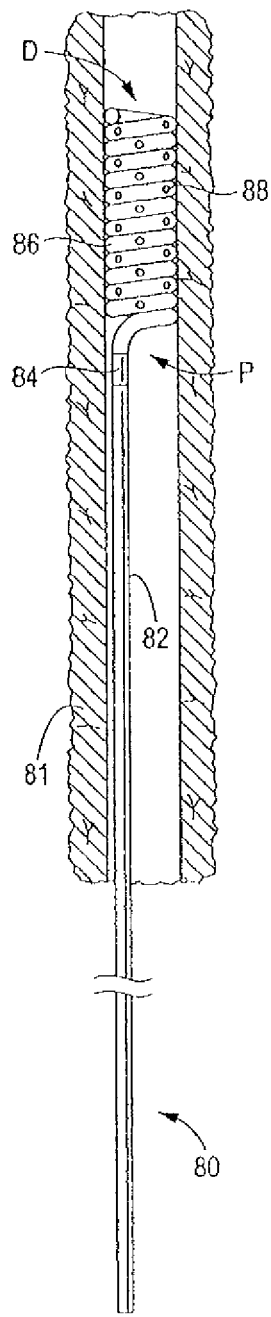
FIG. 8 is an illustration of an exemplary endoluminal device having a detachable supply tube connected thereto.

In another embodiment, shown in FIG. 8, an extension 82 may extend to a location 80 outside of body lumen 81 or at least readily accessible from outside the body lumen. Extension 82 may be used as a tether and/or may be used as a supply tube for injecting a substance into the hollow core of device 86 to be eluted through openings 88 (or through a coating over the openings, as shown in and described with respect to FIG. 6). As shown in FIG. 8, extension 82 may be remotely detachable by providing a predetermined disconnecting segment 84 at the interface between the supply tube and the device 86. In one embodiment, disconnecting segment 84 may include a mechanically weaker circumferential portion of the hypotube that is meant to break at a lesser force than is needed to dislocate the stein from its implanted position. In another embodiment, disconnecting segment 84 may comprise material that electrolytically corrodes preferentially relative to the hypotube material when energized with an electrical current. Various mechanical and electrical mechanisms for providing a removable connection between an endoluminal device and a tether are described generally in U.S. patent application Ser. No. 09/852,524, to Christopher J. Elliot, filed May 10, 2001, assigned to the common assignee of this invention, and incorporated herein by reference. Any of these mechanisms may be applied to the present invention. Segment 84 may also comprise a material this is dissolvable or weakened by a medically acceptable substance that can be injected through extension 82 to render the segment detachable. If a renewable supply of the substance to be eluted from the medical implant is desired over some period of time, the medical implant may have an extension that is left protruding from the body for some period of time to be used as a supply tube. The use of tubes protruding from the body for a period of time for use in supplying medicine to an internal location is well known in the art. When the connection is no longer desired, extension 82 is then severed from device 86 at disconnecting segment 84 by applying mechanical force, electrical current, or both.

Figure 9:
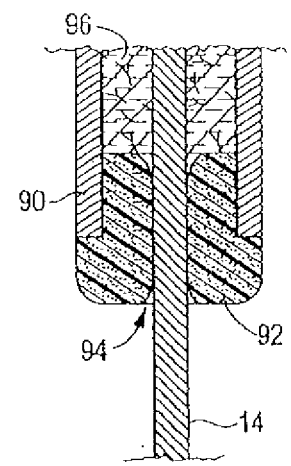
FIG. 9 is an illustration of a tubular member having a plug at its proximal end.

In another embodiment, such as is shown in FIG. 9, a tubular member 90 may not have any openings, such that the tubular member can permanently contain the substance even after the device is deployed. In an embodiment such as is shown in FIG. 9, where the tubular member 90 also is adapted to be advanced over a guidewire 14, the member may comprise a plug 92 at one or both ends of the member, such as a silicone plug with a self-sealing slit 94 that contains the substance 96 but allows the member to slide on the guidewire. When guidewire 14 is pulled through slit 94, the slit seals itself.

Figure 10:
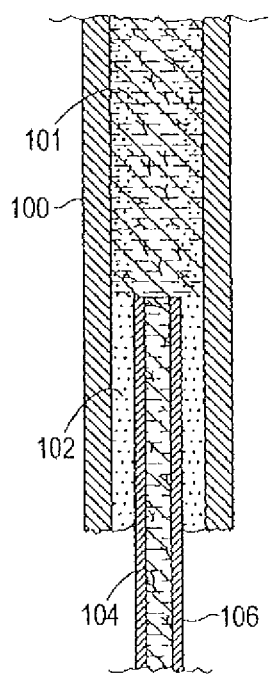
FIG. 10 is an illustration of a tubular member having its distal end filled with a substance.

In another embodiment, shown in FIG. 10, the substance may comprise a two-part resin 101 such as are known in the art of aneurysm occlusion. Thus, member 100 may be partially filled with a first part 102 of two-part resin 101 during delivery to the body, and the second part 104 injected after the member has been delivered into the deployment location. For example, member 100 may be advanced over a hollow-core guidewire 106, such as are known in the art, and the second part 104 of two-part resin 101 may be delivered via the guidewire before it is completely retracted from inside of the member. For example, the second part 104 may be injected as the member 100 is advanced off the end of guidewire 106, forming the combined resin 101 in the void created by the absence of the guidewire.

Figure 1C:
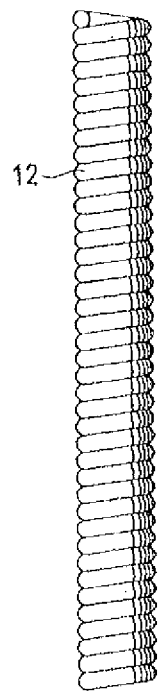
FIG. 1C is a plan view of the device and system of FIG. 1B after full deployment of the device and removal of the guidewire.
Figure 1D:
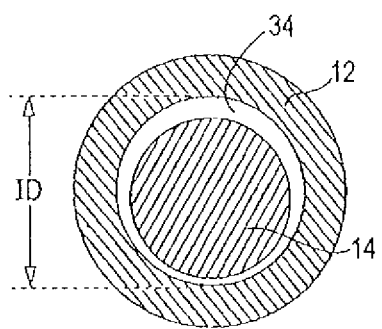
FIG. 1D is a cross-sectional view of the device of FIG. 1A, taken across arrows 1D-1D.
Figure 11:
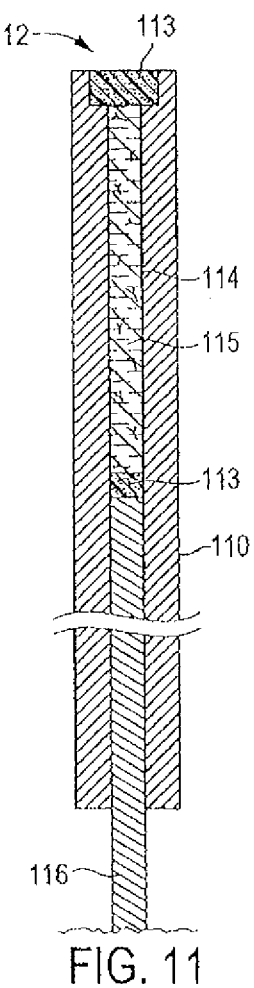
FIG. 11 is an illustration of a tubular member that is partially filled with a first substance.

In embodiments comprising multiple hollow members where not all of the members are used for advancement over guidewires, the members may be filed with the substance and sealed prior to delivery into the body. Even members that are at least partially advanced over guidewires may have an end portion that is partially filled with a substance, such as a contrast agent for marking the end of the device. Thus, for example, as shown in FIG. 11, member 110 may be hollow with a sealed distal end 112 comprising substance 114, such as for example, a contrast agent to make the stent more visible by imaging techniques. Because of the sealed end 112, member 110 and guidewire 116 may be advanced together into the body lumen until the end 112 reaches a desired destination point, and then guidewire 116 may be removed so that the member can deploy, for example, into a configuration similar to that as shown in FIG. 1C. End 112 may be sealed with a plug 113, such as a plug of silicone, and a similar plug may be provided at the proximal end of the chamber 115 containing substance 114, or the substance may comprise a resin that is self-sealing, such as a 2-part resin as described above.

Exemplary types of substances for use in sealed tubular members may include radioactive substances for providing localized radiation treatment, or a contrast agent as described above. The substance may also comprise a material that changes in viscosity or state after implantation into the body. By "changes in viscosity or state" it is meant that the material undergoes a change that affects the rigidity of the combination of the hypotube and substance contained therein. While in one embodiment the change in state may comprise a change from a liquid to a solid, it may also include a change from a first viscosity to a second viscosity sufficient to affect the rigidity of the combined hypotube with the substance inside. Typically, the desired result is to provide a stent that is more rigid after implantation, so the desired change in state is from a lesser viscosity to a greater viscosity. The change in state is not limited to any particular direction of change, however, and may go in the opposite direction if such a result is desired. In one embodiment, for example, the substance may comprise an adhesive such as a cyanoacrylate or polyethylene glycol that hardens when exposed to liquid. The liquid may be provided by a hollow guidewire in a similar manner as the second part of the 2-part resin is supplied as described above, or the liquid flowing in the body lumen may merely seep into the tubular member through open ends of the member, or through holes in the tubular member that are designed to let body liquid in rather than to let the substance in the member out.

In another embodiment, the substance may harden over time after exposure to the internal temperature of the body into which it is implanted, but remains fluid at lower or higher temperatures. Thus, the device must merely be kept at a higher or lower temperature until implantation in the body to prevent premature curing. The hypotube may be completely filled with the substance or partially filled, and the extent to which the hypotube is filled may take into consideration any expansion or contraction in volume of the substance upon the change in state or viscosity.

Figure 12:
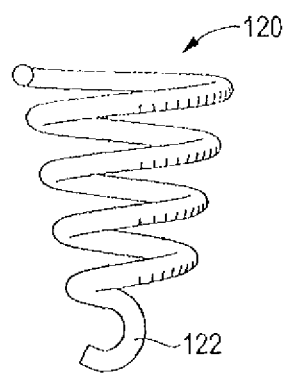
FIG. 12 is an illustration of an exemplary filter.
Figure 13:
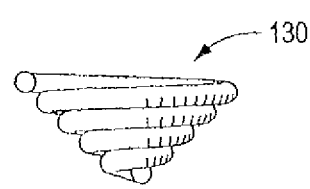
FIG. 13 is an illustration of an exemplary occlusion coil.

Similarly, although described herein with respect to a stent, the invention is not limited to stents, which may be covered with graft material or uncovered, but may include other endoluminal devices such as occlusion devices, valves, coils, and filters, such as vena cava filters. A filter, for example, may comprise a helical coil having a generally conical envelope 120, such as shown in FIG. 12. As is well-known in the art, a helical pitch for a filter is sufficiently wide to let blood flow through but sufficiently narrow to catch any loose thrombus, and having a hook 122 for ease of recapture. Occlusion devices, such as device 130 shown in FIG. 13, are also sometimes referred to as "occlusion coils," "embolic coils," or "wire clusters," and may be used, for example, to close off a portion of a lumen, such as when deploying a uni-aorto-iliac device, as is known in the art. Such devices may also comprise helical coils having a generally conical envelope, but having a pitch so narrow that emboli form to occlude blood flow through the device. Endoluminal devices such as stents having attached grafts may be in the form of single lumen devices, or multi-lumen, branched devices, such as bifurcated devices for repair of abdominal aortic aneurysms (AAA).

The filamentary members described herein may comprise any suitable material known in the art for medical implantation, such as but not limited to nickel-titanium alloys, cobalt-chromium alloys such as elgiloy, stainless steel, and titanium. For tubular members having a shape-memory configuration, nitinol is preferred. For the shape-memory tubular members, it may be preferable for the $A_f$ Temperature (the temperature at which the shape memory alloy finishes transforming to Austenite upon heating) to be slightly greater than standard body temperature, to reduce friction and deflection of the guidewire during deployment of the device. To finalize deployment, the tubular member may be transformed to the shape memory configuration by using a warm flush of saline, such as injected via a hollow-core guidewire.

Just as multi-filament stents may comprise some mix of tubular members and non-tubular members, and the tubular members may comprise some mix of guidewire-advancing and non-guidewire-advancing members, the tubular members may also comprise some mix of members filled and unfilled with one or more substances. Different members may be filled with different substances. Some may not be filled at all. Similarly, an exemplary device may comprise at least one portion comprising a hypotube with one or more openings adapted to elute a first substance contained therein and one portion comprising a hypotube without openings and adapted to permanently contain a second substance therein. Thus, for example, a single implant may have both the ability to deliver a substance to the body and undergo a change in state upon implantation in the body, provide radioactive therapy, or provide enhanced imaging.

The novel structures of this invention also give rise to novel methods of use. For example, one method comprises providing a delivery system comprising a guidewire having an outer diameter, and a self-expanding endoluminal device comprising at least one tubular filamentary member, in which the tubular filamentary member has a straightened configuration for mounting on the guidewire and a shape memory configuration for deployment in the body lumen, as shown in FIGS. 1A-1D. Next, at least the guidewire is advanced into the body lumen to a deployment location, and the guidewire is used for deploying the tubular filamentary member in its shape-memory configuration into the deployment location. In one embodiment, the guidewire may be advanced with the tubular filamentary member mounted on it, such that the deployment step comprises retracting the guidewire and/or advancing the tubular filamentary member off of a distal end of the guidewire into the deployment location. In another embodiment, the guidewire may be advanced without the tubular filamentary member mounted on it, in which the deployment step comprises advancing the tubular filamentary member over the guidewire and off of a distal end of the guidewire into the deployment location.

The method may also comprise injecting a substance into the tubular filamentary member. In certain embodiments, this method further comprises the tubular filamentary member eluting the substance into the body lumen, such as embodiments in which the substance is a biologically or pharmacologically active substance such as but not limited to those discussed above.

In an embodiment in which the endoluminal device comprises a proximal extension of the tubular filamentary member extending to a proximal end outside of the body lumen as shown in FIG. 8, the method comprises injecting the substance into the tubular filamentary member through the proximal extension. Similarly, in an embodiment such as shown in FIG. 8 where the endoluminal device comprises a severable connecting element 84 between proximal extension 82 and endoluminal device 86, the method may further comprise severing the proximal extension from the tubular filamentary member at the severable connecting element. Depending upon the nature of element 84, the severing step may comprise applying a mechanical force and/or applying an electric current originating at or near the proximal end of the proximal extension, or injecting a solvent into the proximal extension to dissolve the severable connecting element.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed is:

1. A self-expanding endoluminal device comprising at least one tubular filamentary member having a proximal end and a hollow core for receiving a guidewire and a graft attached at or near a distal end of the at least one tubular filamentary member, the graft to be deployed and extend proximally from a shape memory configuration at the distal end of the at least one tubular filamentary member, the tubular filamentary member having a straightened configuration for mounting on the guidewire at the proximal end and the shape memory configuration without the guidewire in the hollow core at the distal end, the shape memory configuration attached at or near a distal end of the graft to secure the graft inside a body lumen, the tubular filamentary member comprising a proximal extension having a length sufficient for a proximal end of the extension to be positioned in a location outside of the body lumen or in a location readily accessible from outside of the body lumen with the distal end of the tubular filamentary member in the deployment location.

2. The endoluminal device of claim 1, wherein the tubular filamentary member hollow core is adapted to permanently contain a substance.

3. The endoluminal device of claim 1, wherein the tubular filamentary member hollow core is adapted to receive a substance and to elute the substance from the hollow core.

4. The endoluminal device of claim 3, wherein the tubular filamentary member is coated with a coating material, wherein the coating material comprises (a) a material that the substance within the tubular filamentary member hollow core is capable of leaching through, (b) a material comprising the at least one biologically or pharmacologically active substance, or (c) both (a) and (b).

5. The endoluminal device of claim 1 further comprising a severable connecting element between the proximal extension and the endoluminal device.

6. The endoluminal device of claim 5, wherein the connecting element is severable through application of a mechanical force originating at or near the proximal end of the proximal extension.

7. The endoluminal device of claim 5, wherein the connecting element is severable through application of an electric current originating at or near the proximal end of the proximal extension.

8. The endoluminal device of claim 5, wherein the connecting element is severable through dissolution by injection of a solvent into the tubular filamentary member.

9. The endoluminal device of claim 1, wherein the endoluminal device comprises a plurality of filamentary members attached together.

10. The endoluminal device of claim 9, wherein the device comprises a single tubular filamentary member and a plurality of non-tubular filamentary members.

11. An endoluminal device and delivery system for deploying the endoluminal device in a body lumen from a proximal point outside of the body lumen, the endoluminal device and delivery system comprising:
   at least one guidewire; and
   the endoluminal device of claim 1.

* * * * *